| United States Patent [19] | [11] 4,224,297 |
|---|---|
| Straussberger et al. | [45] Sep. 23, 1980 |

[54] METHOD FOR REACTIVATING A RESIDUE CONTAINING ELEMENTAL SILICON

[75] Inventors: Herbert Straussberger; Willi Streckel; Rudolf Riedle, all of Burghausen, Fed. Rep. of Germany

[73] Assignee: Wacker-Chemie GmbH, Munich, Fed. Rep. of Germany

[21] Appl. No.: 906,714

[22] Filed: May 17, 1978

[30] Foreign Application Priority Data

Jul. 22, 1977 [DE] Fed. Rep. of Germany ....... 2733290
Feb. 24, 1978 [DE] Fed. Rep. of Germany ....... 2807951

[51] Int. Cl.² .................. C01B 33/02; B01J 37/00
[52] U.S. Cl. .................. 423/348; 252/411 R; 252/416

[58] Field of Search ................. 423/342, 348; 260/448.2 T; 252/411 R, 416

[56] References Cited

U.S. PATENT DOCUMENTS 2,389,931  11/1945  Reed et al. ............. 260/448.2 T
3,645,686  2/1972  Tucker ..................... 423/348

*Primary Examiner*—Jack Cooper

[57] ABSTRACT

A method for utilizing a residue containing elemental silicon in the form of particles having a maximum diameter of 50 microns which comprises heating the residue for at least 15 hours at a temperature of from 100° to 350° C. in the presence of atmospheric air and/or an inert gas and thereafter recycling the treated residue into a process for preparing halosilanes.

4 Claims, No Drawings

METHOD FOR REACTIVATING A RESIDUE CONTAINING ELEMENTAL SILICON

The present invention relates to the utilization of a residue containing elemental silicon and more particularly to a method for treating a residue containing elemental silicon and its utilization in the preparation of halosilanes.

BACKGROUND OF THE INVENTION

It has been known that silicon halides and more particularly organosilicon halides can be prepared by effecting a reaction between organic halides, especially hydrocarbon halides and a silicon component of a solid, porous contact mass containing silicon and a metallic catalyst for the reaction at elevated temperatures. However, over a period of time, the hydrocarbon halides and the hydrocarbon substituted silicon halides will pyrolyze to a certain degree at the reaction temperatures. This results in the formation of hydrocarbons and gums which gradually coat the silicon particles and bring the reaction to an end. The resultant solid porous contact mass containing up to about 40 percent by weight of inorganic substances other than elemental silicon is often referred to as a "dead bed" or "spent" residue. Generally, the "spent" residue which contains elemental silicon particles having a maximum diameter up to about 50 microns was sent to a smelting process or it was discarded.

When the "spent" residue was discarded, it would contaminate the environment and when the residue was treated by the smelting process, large amounts of energy were required. Thus, it has been found that the "spent" residue can now be reactivated and reused in the preparation of silicon halides without contaminating the environment and without expending large amounts of energy.

Therefore, it is an object of this invention to provide a process for reactivating a "spent" residue containing elemental silicon. Another object of this invention is to provide a method for reactivating a residue without having to consume large amounts of energy. A further object of this invention is to provide a method for utilizing a residue containing elemental silicon in the preparation of silicon halides.

SUMMARY OF THE INVENTION

The foregoing objects and others which will become apparent from the following description are accomplished in accordance with this invention, generally speaking, by providing a method for reactivating a "spent" residue containing elemental silicon having a maximum particle diameter of about 50 microns which comprises heating the residue in atmospheric air and/or an inert gas at a temperature of from about 100° to 350° C. for at least 15 hours and thereafter recycling the treated residue to a process for preparing halosilanes or hydrocarbon-substituted halosilanes by contacting the same with hydrocarbon halides and/or hydrogen halides.

DETAILED DESCRIPTION OF INVENTION

The reaction residue or "spent" residue utilized in this invention contains silicon particles having a maximum diameter of about 50 microns. This residue is obtained by separating the gaseous or liquid substances formed as a result of the reaction of hydrocarbon halides and/or hydrogen halides with a solid porous contact mass containing silicon.

The halogen atoms in the hydrocarbon halides which are reacted with the silicon containing contact mass from which the reaction residue is obtained are fluorine, chlorine, bromine or iodine atoms. Chlorine is the preferred atom since it is readily available.

The hydrocarbon radicals in the hydrocarbon halides which are reacted with the silicon containing contact mass from which the reaction residue is obtained are alkyl radicals, such as the methyl, ethyl, propyl, butyl as well as the octadecyl radicals, cycloalkyl radicals such as cyclopropyl, cyclobutyl, cyclohexyl and cyclooctyl radicals, alkenyl radicals such as ethenyl, propenyl, butenyl, hexenyl and octenyl radicals; cycloalkenyl radicals such as the cyclohexyl-ethenyl, cycloheptyl-propenyl and cyclooctyl-propenyl radicals; alkinyl radicals; aryl radicals such as the phenyl radical, alkaryl radicals such at the tolyl, xylyl, cumenyl and ethylphenyl radicals and the aralkyl radicals such as the benzyl, phenyl-ethyl, phenyl-propyl and phenyl-butyl radicals. The methyl radical is preferred radical because it is readily available.

The silicon employed in the reaction with the hydrocarbon halides and/or HCl is generally alloyed with iron and contain metals or metal compounds either as alloys or in admixture. Those metal compounds serve to catalyze the reaction of the silicon with the hydrocarbon halides and/or to force the reaction in the desired direction. Examples of such metals or metal compounds are copper, zinc chloride and zirconium chloride. Consequently, the reaction residue used pursuant to this invention contains for example copper and iron, partly in the form of volatile chlorides, in addition to elemental silicon and possibly carbon which is formed as a result of the pyrolysis or dissociation of the hydrocarbon halides and/or the products resulting from the reaction of hydrocarbon halides with silicon.

The reaction of the hydrocarbon halides, especially methyl chloride and/or HCl with silicon is preferably carried out using a fluidized bed in order to precisely control the temperature.

The separation of the reaction residue from the gaseous substance generated during the reaction of the hydrocarbon halides and/or HCl with silicon can be achieved through centrifugation, for example in a so-called cyclone. The reaction residue utilized in this invention can be separated from a liquid substance resulting from the reaction of the hydrocarbon halides and/or HCl with silicon, for example, by filtration.

It is preferred that the reaction residue obtained after the gaseous or liquid substances have been separated, be heated for from 20 to 80 hours at temperatures of from 100° to 350° C. and more preferably at temperatures of from 100° to 200° C.

Because of its availability and because it is inert at the temperatures used, nitrogen is the preferred inert gas.

The process of this invention provides a means to reactivate a "spent" reaction residue containing silicon particles having a maximum diameter of 50 microns which has been obtained from the reaction of hydrocarbon halides and/or HCl with silicon by heating the "spent" residue at a temperature of from 100° to 350° C. for at least 15 hours in the presence of a gaseous medium such as atmospheric air and/or an inert gas.

Moreover, the method of this invention permits recycling of the treated residue in the form of silicon particles having a maximum diameter of 50 microns into a process where the silicon is treated with HCl to form for example trichlorosilanes.

Also, the method of this invention makes it possible to reuse a reaction residue containing silicon particles having a maximum diameter of 50 microns which was previously employed in a reaction with hydrogen halides, by heating the residue which has been separated from gaseous or liquid substances, at a temperature of from about 100° to 350° C. for at least 15 hours in the presence of atmospheric air and/or an inert gas and thereafter recycling the treated residue to a reactor where it is contacted with hydrocarbon halides and possibly hydrogen halides.

For economical reasons, the process of this invention is preferably carried out at atmospheric pressure, i.e. 760 mm Hg (abs.) or at approximately 760 mm Hg (abs.). However, if desired, higher or lower pressures may be used.

In the reaction of hydrocarbon halides and/or HCl with silicon, it is possible to use the reaction residue treated in accordance with this invention together with other waste materials which contain elemental silicon in the form of particles having a maximum diameter of 50 microns. Examples of such other waste materials are those that are generated during reactions other than by hydrocarbon halides with silicon such as for example during the process in which copper is recovered from used-up silicon and a copper containing contact mass, where such waste materials may still contain water as well as particles containing elemental silicon having a maximum diameter of 50 microns which are obtained from the pneumatic conveyor. Other waste materials which may be mixed with the treated residue are the undesirable fine particles which are generated as a by product in the grinding process for preparing granular silicon to be used in the fluidized bed process for synthesizing organohalosilanes or trichlorosilanes.

In the following examples all precentages are by weight unless otherwise specified.

EXAMPLE 1

About 120 grams of reaction residue which contains elemental silicon in the form of particles having a maximum diameter of about 50 microns which were separated from the gaseous substance obtained during the reaction of methyl chloride with silicon, are heated for 70 hours in atmospheric air at a temperature of from 120° to 140° C. and then placed in a vertical glass reactor. With constant agitation by means of a mechanical stirrer, the powder is heated in the glass reactor to 320° C., while 460 grams of gaseous methyl chloride is passed through the powder from the bottom through a sintered glass filter plate over a period of 4 hours. The gaseous silane mixture exiting from the top of the glass cylinder is condensed, weighed and analyzed by gas chromatography.

EXAMPLE 2

The process described in Example 1 is repeated, except that a mixture containing 60 grams of the same reaction residue and 60 grams of waste in the form of particles having a maximum diameter of 50 microns which were obtained during the process in which copper is recovered from used-up silicon and a copper-containing contact mass, and also contains silicon as well as approximately 1 percent by weight of water is substituted for the 120 grams of reaction residue obtained from the reaction of methyl chloride with silicon.

EXAMPLE 3

The process described in Example 1 is repeated, except that a mixture containing 60 grams of the reaction residue and 60 grams of the undesirable fine particles which are generated as a byproduct in the grinding process for preparing granular silicon to be used in the fluid bed process for synthesizing organohalogensilanes or trichlorosilanes is substituted for the 120 grams of reaction residue obtained from the reaction of methyl chloride with silicon.

COMPARATIVE EXAMPLE (a)

The process described in Example 1 is repeated, except that following the separation of the gaseous substance, the reaction residue is merely cooled under nitrogen and then reacted with methyl chloride without further treatment.

COMPARATIVE EXAMPLE (b)

The process described in Example 2 is repeated, except that the mixture of reaction residues is reacted with methyl chloride without further treatment.

The following Table shows the results obtained:

TABLE

|  | Examples | | | Comparative Examples | |
|---|---|---|---|---|---|
|  | 1+ | 2+ | 3++ | (a)+ | (b)+ |
| Total Amount of Organochlorosilane in grams | 232 | 200 | 200 | 248 | 168 |
| Dimethyldichlorosilane Percent | 82.0 | 87.5 | 82.8 | 68.3 | 72.9 |
| Methyltrichlorosilane Percent | 13.3 | 9.7 | 10.7 | 21.6 | 22.5 |
| Trimethylchlorosilane Percent | 3.5 | 1.6 | 3.4 | 8.3 | 3.7 |
| Methyldichlorosilane Percent | 1.2 | 1.2 | 3.1 | 1.8 | 0.9 |

+ Average values obtained from at least six identical procedures.
++ Average values from three identical procedures.

EXAMPLE 4

The process described in Example 3 is repeated, except that 460 grams of HCl is passed through the powder within 4 hours instead of methyl chloride.

| Result: | | | |
|---|---|---|---|
| Total amount of chlorosilane in grams | $SiCl_4$ percent | $SiHCl_3$ percent | $SiH_2Cl_2$ percent |
| 400 | 4.9 | 95.0 | 0.1 |

What is claimed is:

1. A method for reactivating a residue containing particles of elemental silicon having a maximum diameter of 50 microns which has been recovered from the reaction of a halogen containing compound selected from the group consisting of hydrocarbon halides, hydrogen halides and mixtures thereof with a solid porous contact mass containing silicon to form silicon halides, which comprises heating the residue containing elemental silicon to a temperature of from 100° to 350° C. for from 20 to 80 hours in the presence of a gaseous medium selected from atmospheric air, nitrogen and mixtures thereof.

2. The method of claim 1, wherein the residue is heated to a temperature of from 100° to 200° C.

3. The method of claim 1, wherein the gaseous medium is atmospheric air.

4. The method of claim 1, wherein the gaseous medium is nitrogen.

* * * * *